(12) United States Patent  
Schuessler et al.

(10) Patent No.: US 8,449,474 B2  
(45) Date of Patent: May 28, 2013

(54) SELF-ACTUATED CYLINDER AND OSCILLATION SPIROMETER

(75) Inventors: Thomas Schuessler, Ville Mont-Royal (CA); Ilan Benjamin Urovitch, Cote-Saint-Luc (CA)

(73) Assignee: Scireq Scientific Respiratory Equipment Inc., Montreal, Quebec (CA)

( * ) Notice: Subject to any disclaimer, the term of this patent is extended or adjusted under 35 U.S.C. 154(b) by 1342 days.

(21) Appl. No.: 11/994,280

(22) PCT Filed: Jun. 28, 2006

(86) PCT No.: PCT/CA2006/001071  
§ 371 (c)(1), (2), (4) Date: Sep. 24, 2008

(87) PCT Pub. No.: WO2007/000052  
PCT Pub. Date: Jan. 4, 2007

(65) Prior Publication Data  
US 2009/0253994 A1   Oct. 8, 2009

(30) Foreign Application Priority Data

Jun. 29, 2005  (CA) ..................................... 2511070

(51) Int. Cl.  
*A61B 5/091* (2006.01)  
*F04B 35/04* (2006.01)  
*F15B 21/02* (2006.01)

(52) U.S. Cl.  
USPC .............................. 600/538; 417/415; 91/359

(58) Field of Classification Search  
None  
See application file for complete search history.

(56) References Cited

U.S. PATENT DOCUMENTS

| 5,856,745 | A | | 1/1999 | Morgan et al. |
| 5,975,748 | A | * | 11/1999 | East et al. ......................... 703/6 |
| 6,049,146 | A | * | 4/2000 | Takara ............................ 310/24 |
| 2004/0208761 | A1 | | 10/2004 | Bader |

* cited by examiner

*Primary Examiner* — Shanon A Foley  
(74) *Attorney, Agent, or Firm* — Choate, Hall & Stewart LLP; Charles E. Lyon; Daniel S. Matthews

(57) ABSTRACT

A self-actuated cylinder comprising a cylinder housing comprising electro-magnetic force generating means to generate electro-magnetic forces, and a piston within the cylinder housing, wherein the electro-magnetic forces act directly on the piston to displace the piston within the cylinder housing. The self-actuated cylinder can be used as an oscillation spirometer to determine air flow, an input impedance or Forced Oscillation pulmonary mechanics.

8 Claims, 3 Drawing Sheets

SELF-ACTUATED CYLINDER AND OSCILLATION SPIROMETER

FIELD OF THE INVENTION

The present invention relates to a self-actuated cylinder for use in several kinds of equipment, including integrated devices for spirometry and forced oscillation pulmonary mechanics.

BACKGROUND OF THE INVENTION

There is a general interest in servo-controlled piston/cylinder pumps. For example, SCIREQ's flagship product, the flexiVent™, is essentially a computer-controlled piston pump that is customized for use as a mechanical ventilator and measuring device of pulmonary mechanics for pre-clinical research.

Servo-controlled piston pumps typically consist of i) an actuator, ii) a piston/cylinder assembly, iii) a position/displacement measurement device, and iv) gears, rods or other means of connecting the other components together in order to transmit force from one component to the other. While in some cases, the actuator and the position measurement are somewhat integrated, e.g. when a stepper motor is used, there is no known solution in the public domain that combines the actuator and the cylinder into a single device in such a way that there is no need for connecting rods or gears whatsoever.

The arrangements described above have a number of disadvantages. First, their size cannot easily be minimized because space must be provided for the connecting rods. For example, a setup based on a DC linear actuator can easily require an overall length that is greater than four times its actual stroke length, Furthermore, the connecting gears and rods can pose problems and/or reduce performance due to weight, insufficient stiffness, poor alignment, play in joints, friction and dynamic properties, Finally, the multiplicity of components adds to the overall system cost.

Thus, there is still presently a need for development of a self-contained linear actuator/cylinder that would integrate a linear actuator, a cylinder to displace gases or liquids and means to measure position into a single device that i) does not require any connecting rods or gears; and ii) fits into a smaller envelope that conventional actuator/cylinder assemblies with comparable stroke volume.

Additionally, there is a need for an improved integrated device for spirometry and forced oscillation pulmonary mechanics. In pulmonary medicine, the breathing pattern of a patient is often quantitatively assessed by recording the airflow at the patient's mouth and/or nose and deriving a number of parameters such as tidal volume and breathing frequency. Often, the patient is also asked to perform specific manoeuvres such as a deep inflation followed by a hard expiration in order to measure the forced expired volume in one second ($FEV_1$) and the forced vital capacity (FVC). This process is commonly referred to as "spirometry".

In recent years, a technique known as the Forced Oscillation Technique (FOT) has emerged as a possible alternative to spirometry. Briefly, the FOT measures the input impedance of the respiratory system, typically in the frequency band from sub-acoustic frequencies to roughly 50 Hz, by imposing small amplitude waveforms onto the subject's airway opening. The resulting flows and pressure swings are recorded and used to calculate the real and imaginary parts of the input impedance. Devices to obtain FOT measurements in humans are typically based on large loudspeakers that are connected to the subject's airway opening via long tubing. A side port with a calibrated resistance and/or a bias flow ensures that the patients do not re-breathe their own expired air. The resulting airflow is estimated or measured using pneumotachographs.

The FOT has the advantages that it requires less patient cooperation, that it offers detailed information and that the parameters it measures relate directly to the physics of the lungs. However, current FOT devices are limited because of their large size, poor low frequency performance and poor coupling between the patient and the device.

Consequently, there is still presently a need for an "Oscillation Spirometer" (OS) that i) can act both as a spirometer and to obtain FOT measurements; ii) is compact and light enough to be portable and permit handheld operation; iii) places the FOT waveform generator in close proximity of the airway opening to permit good coupling between patient and device; iv) offers good performance down to ultra-low frequencies, and v) can possibly be integrated into a mechanical ventilator circuit.

SUMMARY OF THE INVENTION

An object of the present invention is to propose a self-actuated cylinder that satisfies at least one above-mentioned need.

According to the present invention, that object is achieved with a self-actuated cylinder that integrates a linear electromagnetic actuator, a cylinder and a position sensing device into a single, compact and self-contained device wherein the electromagnetic actuator forces act directly onto the piston head.

More particularly, the present invention provides a self-actuated cylinder comprising:
- a cylinder housing comprising electromagnetic force generating means to generate electromagnetic forces; and
- a piston within the cylinder housing,
  - wherein the electro-magnetic forces act directly on said piston to displace said piston within said cylinder housing.

Preferably, the self-actuated cylinder further comprises a position sensing device for measurement of a position of the piston with respect to the cylinder housing.

In accordance with a preferred aspect of the invention, there is also provided an oscillation spirometer which uses the self-actuated cylinder as defined above. In this preferred embodiment of the self-actuated cylinder, the cylinder further comprises:
- front and rear air chambers within the cylinder housing on opposite sides of the piston;
- a flow pathway to permit airflow between the front and rear air chambers;
- a front cover plate covering the front air chamber, and comprising a front port to allow an exchange of air between the front air chamber and a respiratory system;
- a rear cover plate covering the rear air chamber comprising an interface to allow an exchange of air between the rear air chamber and an external environment; and
- a pressure transducer to measure the pressure drop across the flow pathway, wherein the pressure measurement is used to determine air flow from the port when the piston is held in a forward position, and the pressure and position measurements are used to determine an input impedance of the respiratory system attached to the frontport when the piston oscillates according to a predefined waveform.

A non-restrictive description of preferred embodiments of the invention will now be given with reference to the appended drawings.

DESCRIPTION OF PREFERRED EMBODIMENTS

Figure 1:
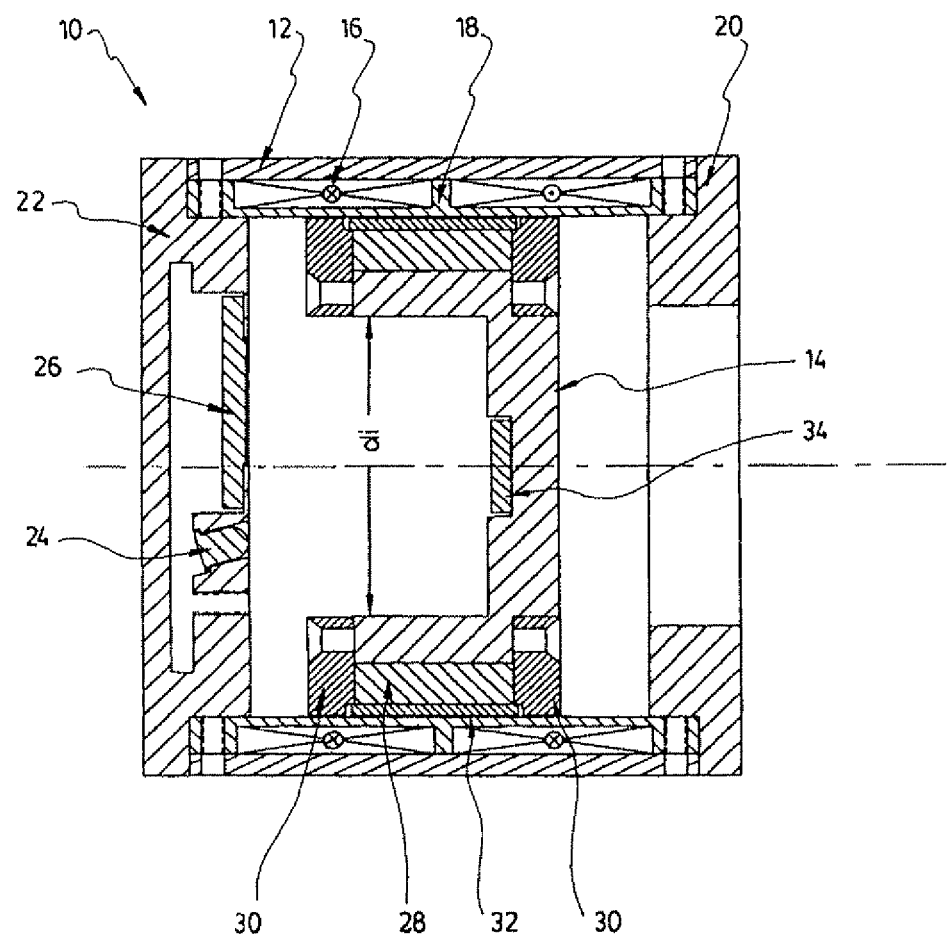
FIG. 1 is a side cross-sectional view of a self-actuated cylinder according to the present invention.
Figures 2, 3:
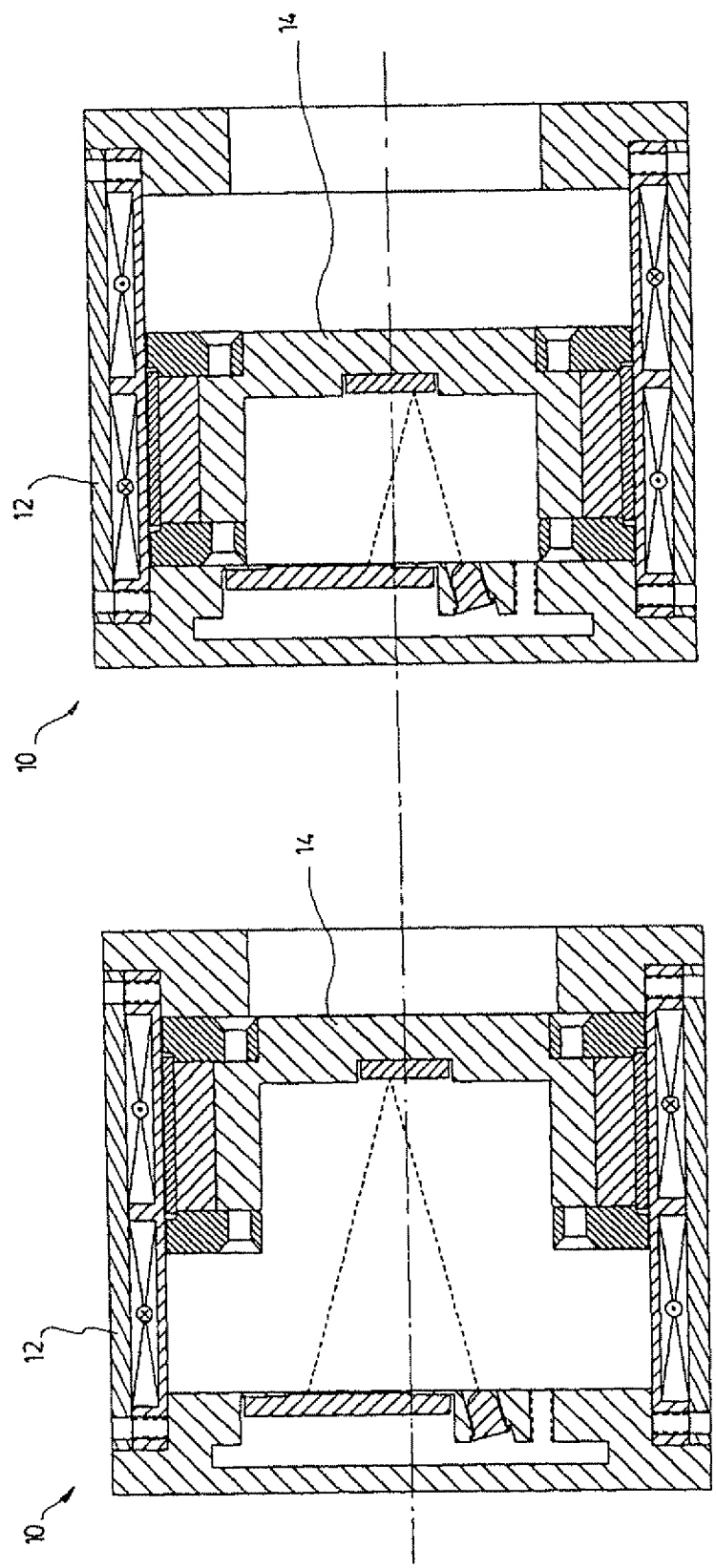
FIG. 2 is side cross-sectional view of the self-actuated cylinder shown in FIG. 1 with the piston in a full forward position.
FIG. 3 is side cross-sectional view of the self-actuated cylinder shown in FIG. 1 with the piston in a full backward position.

Referring to FIGS. 1 to 3, the present invention provides a self-actuated cylinder 10 comprising a cylinder housing 12 comprising electromagnetic force generating means to generate electro-magnetic forces and a piston 14 within the cylinder housing 12, wherein the electro-magnetic forces act directly on the piston 14 to displace the piston 14 within said cylinder housing 12.

The basic concept of the Self-Actuated Cylinder (SAC) is that the force generated by the electromagnetic actuator acts directly on the piston. In other words, one component or assembly acts both as the moving part of the actuator and as the piston. A second component or assembly acts both as the stationary part of the actuator and as the cylinder. Preferably, the transmission of force is based on the principles of a moving magnet linear electro-magnetic actuator. In an alternate embodiment of the present invention, a moving coil design may be used.

In accordance with a preferred embodiment of the present invention, the principal layout of the SAC is illustrated in the cross-section shown in FIG. 1. The stationary assembly consists of a cylinder housing 12 which is preferably an outer ferromagnetic housing; a motor coil 16 that has two sections of copper windings wound or otherwise energized in inverse directions (e.g. the windings are wound in the same direction but have inverse currents); a non-ferrous bobbin 18 that mechanically supports the motor coil, and that may have an internal coating for sealing and/or reduced friction; a frontal cover-plate 20 fitted with holes or ports as required by the specific application; a rear cover plate 22 containing holes or ports as required by the specific application; an off-center laser diode 24 that projects a well-defined laser beam onto the moving parts of the actuator; and an optical position sensing device 26 that reads the reflection of the laser from the moving part. The moving part of the actuator consists of a permanent ring magnet 28 polarized in its axial direction; two ferromagnetic pole plate disks 30 attached to either end of the magnet whose shape and dimensions are such that they can effect a 90 degree redirection of the magnetic field into the radial direction without sharp corners or strangulation of the field; a thin sleeve 32 that fits around the magnet and is held in the axial direction by the pole plates, made from a material or coated on its outside surface for sealing and/or reduced friction; a piston 14 comprising a face and support structure that prevents the exchange of air from one side of the moving part to the other; and a mirror or other reflective surface 34 attached to or integrated in the rear surface of the piston face that is suitable to reflect the light emitted by the laser diode 24 onto different sections of the optical position sensing device 26, depending on the position of the moving part within the stationary part. Both the stationary and the moving part contain screws, o-rings and/or glue joints that maintain the mechanical integrity of the device, but whose exact location and design is inconsequential for the principal operation of the device. Similarly, the aspect ratio and relative dimensions of some of the components of the present dimension may be varied without affecting the operation of the device.

The following design constraints must be met for this device to operate properly. i) The outer diameter of the sleeve 32 and the inner diameter of the bobbin 18, as well as their choice of materials and/or coatings, must be chosen to provide a fit that offers a suitable combination of seat and friction characteristics for any particular application. ii) The outer diameter of the pole plate disks 30 must be less than the outer diameter of the sleeve 32. iii) The inner diameters of the ring magnet 28 and the pole plates 30, as well as the positioning of the laser diode 24 and the optical position sensing device 26 on the rear cover plate 22, must be such that the laser beam can reach and be reflected off the mirror 34 to ultimately reach the optical position sensing device 26 without obstruction over the entire range of possible positions of the moving part within the stationary part (as shown in FIGS. 2 and 3).

In another embodiment of the present invention, electronic circuitry to servo-control the position of the moving part by adequately energizing the motor coil 16 based on the readings from the optical position sensing device 26 can be integrated directly in the body of the SAC. The metallic components of the SAC can act as an adequate heat sink for an integrated power amplifier that is suitable to provide power to the actuator. A miniature signal processing chip can perform the servo-control tasks and can be programmed with individual controller parameters to compensate for small variations between units and assure reproducible performance.

Figure 4:
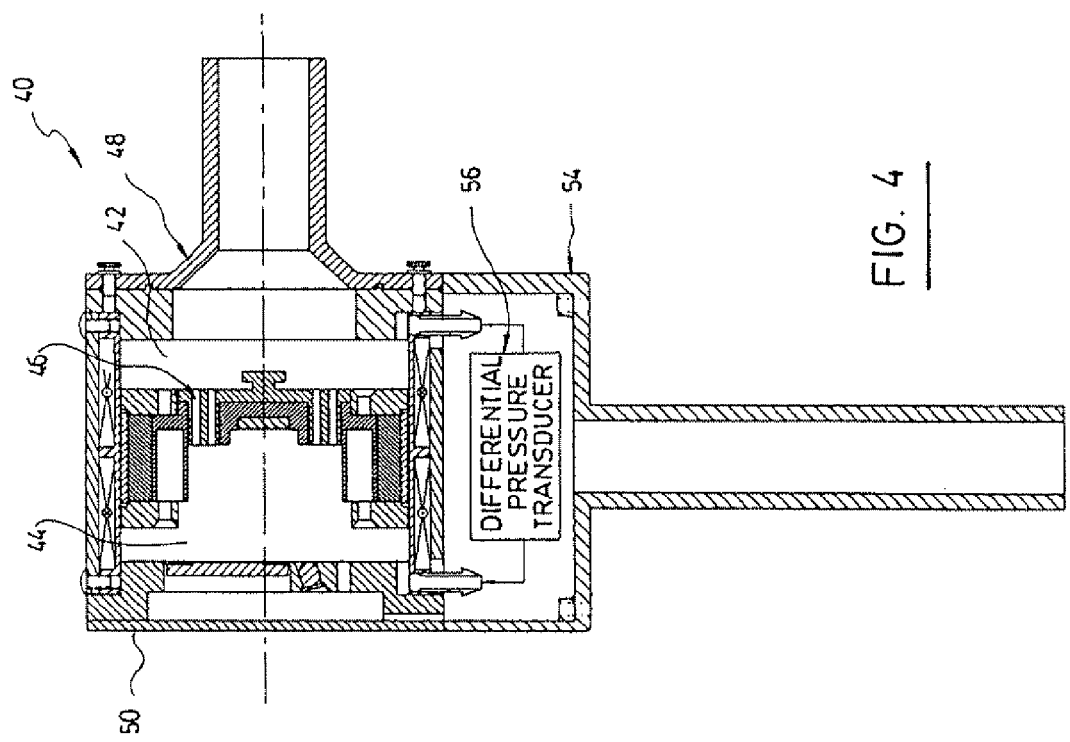
FIG. 4 is a side cross-sectional view of an oscillation spirometer according to a preferred embodiment of the present invention.
Figure 5:
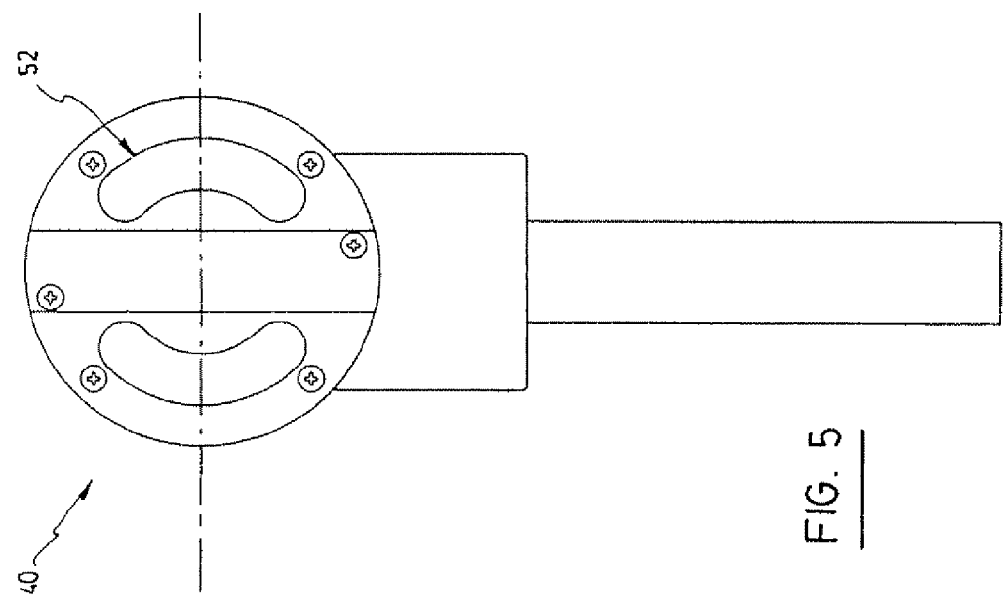
FIG. 5 is a rear view of the oscillation spirometer shown in FIG. 4.

Referring to FIGS. 4 and 5, in accordance with a preferred embodiment of the present invention, there is also provided an oscillation spirometer (OS) 40 which uses the self-actuated cylinder 10 as defined above. In this preferred embodiment of the self-actuated cylinder 10, the cylinder 10 further comprises front 42 and rear 44 air chambers within the cylinder housing 12 on opposite sides of the piston 14. The cylinder 10 further comprises a flow pathway 46 to permit airflow between the front 42 and rear 44 air chambers. The cylinder 10 further comprises a front cover plate 48 covering the front air chamber 42, and comprising a port to allow an exchange of air between the front air chamber 42 and a subject. The port can be a standard clinical port, or a mouth piece, among other things, and may be fitted with a bacterial filter, and may be disposable. The cylinder 10 further comprises a rear cover plate 50 covering the rear air chamber 44 and comprising holes 52 to allow an exchange of air between the rear air chamber 44 and an ambient environment. The cylinder 10 further comprises a handle 54, The handle 54 may be replaced with other mounting or attachment means to link the cylinder to various structures. The cylinder 10 further comprises a pressure transducer 56 to measure the pressure drop across the flow pathway 46. The pressure measurement is used to determine air flow from the clinical port when the piston is held in a forward position and the pressure measurement is used to determine an input impedance of the air flow from the clinical port when the piston oscillates according to a predefined waveform.

The design for the OS 40 is based on the SAC technology described above, As mentioned previously, the SAC integrates a linear actuator, a cylinder and a position sensing device into a single, compact and self-contained device where the electromagnetic actuator forces act directly onto the piston head.

For the OS, the SAC design was modified as shown in FIG. 4, as follows. A) A flow pathway 46 was added to permit airflow between the two sides of the moving part. This pathway 46 must offer a resistance to flow that is stationary and sufficiently linear that it is mathematically reversible, so that the instantaneous flow rate can be calculated from the pressure drop across this pathway 46. In the current design, this pathway is achieved by means of precision holes in the piston face plate; however, the pathway could in principle also be achieved in other locations, e.g. via precision longitudinal grooves in the outer surface of the moving part. B) The frontal cover plate 48 was modified to hold an anti-bacterial filter and provide a standard clinical port C) The rear cover plate 50 was modified to include sufficiently large holes 52 that the air to in the rear section of the actuator is easily exchanged with ambient air by means of diffusion. D) In an alternate design, the rear cover plate 50 was modified to provide a standard clinical port for integration into a ventilator circuit. E) A handle 54 with room for electronic circuitry was added. F) A differential pressure transducer 56 was included in the electronic circuitry, such that the ports of the differential pressure transducer communicate with the two sides of the moving part of the actuator and hence measure the pressure drop across the flow pathway 46. G) A second transducer was added to measure the pressure on the frontal side of the piston with respect to atmosphere. This transducer is redundant and can be omitted in cases where the rear air chamber 44 is at atmospheric pressure, so that transducer 56 effectively takes on the function of the second transducer as well.

For spirometry measurements, this device can act as a standard flow meter when the moving part is held in a forward position while the subject breathes through a mouthpiece attached to the port in the frontal cover plate 48. The flow is calculated from the differential pressure measured using the transducer 56 and the resistance of the flow pathway 46 that is known from a factory calibration manoeuvre.

For FOT measurements, the moving part of the OS 40 oscillates according to a predefined waveform. Depending on the exact nature of the desired measurements, the subject may either be breathing spontaneously or remain passive with an open glottis. In the first case, measurements can only be easily obtained at frequencies that are not strongly represented in the power spectrum of the spontaneous respiration.

During an oscillation, the position of the piston and hence the volume displaced by the piston is constantly measured. As the piston displaces a certain volume $\Delta V_0$ towards the subject, this volume will split into three components. One part of the $\Delta V_0$ will enter the airways of the patient ($\Delta V_P$); a second part will cause compression of the gas in the volume between the piston face and the patient's airway opening ($\Delta V_C$) to a certain airway opening pressure ($P_{aw}$) that is captured by the second transducer (or the first transducer 56, as the case may be); a third part of $\Delta V_0$ will flow through the pathway 46 and escape to atmosphere ($\Delta V_L$). Therefore, the volume that enters the patient can be expressed as $$\Delta V_P = \Delta V_0 - \Delta V_C - \Delta V_L \quad (1)$$

As for spirometry, $\Delta V_L$ is can be calculated from the pressure measured by the transducer 56 and the resistance properties of the flow pathway 46. Also, the relationship between $P_{aw}$ and $\Delta V_C$ depends solely on the geometry of the equipment and can hence be analytically or experimentally determined and subsequently be used to calculate the instantaneous value of $\Delta V_C$. Consequently, all quantities on the right hand side of Equation 1 are known, so that the left hand side can be calculated. Since $P_{aw}$ has also been measured, the input impedance of the subjects respiratory system can be calculated from the data collected by the OS 40 as the ratio of $P_{aw}$ and $V'_P$ at any given frequency of interest, where $V'_P$ is derivative of $V_P$ over time and is commonly referred to as flow.

Although the present invention has been explained hereinabove by way of preferred embodiments thereof, it should be understood that the invention is not limited to these precise embodiments and that various changes and modifications may be effected therein without departing from the scope or spirit of the invention.

What is claimed is:

1. A self-actuated cylinder comprising:
   a cylinder housing comprising electro-magnetic force generating means to generate electro-magnetic forces;
   a piston within the cylinder housing;
   a position sensing device for measurement of a position of the piston with respect to the cylinder housing;
   front and rear air chambers within the cylinder housing on opposite sides of the piston;
   a flow pathway to permit airflow between the front and rear air chambers;
   a front cover plate covering the front air chamber, and comprising a front port to allow an exchange of air between the front air chamber and a respiratory system;
   a rear cover plate covering the rear air chamber comprising an interface to allow an exchange of air between the rear air chamber and an external environment; and
   a pressure transducer to measure a pressure drop across the flow pathway,
   wherein the electro-magnetic forces act directly on said piston to displace said piston within said cylinder housing, and the pressure measurement is used to determine air flow from the front port when the piston is held in a forward position, and the pressure and position measurements are used to determine an input impedance of the respiratory system attached to the front port when the piston oscillates according to a predefined waveform.

2. The self-actuated cylinder according to claim 1, wherein the interface comprises holes and the external environment is an ambient environment.

3. The self-actuated cylinder according to claim 1, wherein the interface comprises a rear port and the external environment is a ventilator circuit.

4. The self-actuated cylinder according to claim 1, further comprising:
   a second pressure transducer for measurement of a pressure difference between the front air chamber and atmosphere.

5. The self-actuated cylinder according to claim 1, wherein the piston comprises a reflective surface on a rear surface thereof and the position sensing device comprises:
   an off-center laser diode projecting a laser beam onto the reflective surface; and
   an optical position sensor receiving the reflected laser beam.

6. The self-actuated cylinder according to claim 5, further comprising:
   electronic circuitry to servo-control the position of the piston by energizing the electro-magnetic force generating means based on readings from the position sensing device.

7. The self-actuated cylinder according to claim 1, wherein the front port is fitted with an anti-bacterial filter.

8. The self-actuated cylinder according to claim 1, further comprising attachment means for attaching the cylinder to an external structure.

* * * * *

UNITED STATES PATENT AND TRADEMARK OFFICE
CERTIFICATE OF CORRECTION

PATENT NO. : 8,449,474 B2 Page 1 of 1
APPLICATION NO. : 11/994280
DATED : May 28, 2013
INVENTOR(S) : Schuessler et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1551 days.

Signed and Sealed this
Eighth Day of September, 2015

Michelle K. Lee
*Director of the United States Patent and Trademark Office*